(12) United States Patent
Vilallonga et al.

(10) Patent No.: US 8,906,642 B2
(45) Date of Patent: Dec. 9, 2014

(54) METHODS AND COMPOSITIONS FOR THE TREATMENT AND DIAGNOSIS OF HAEMORRHAGIC CONVERSION

(75) Inventors: Joan Montaner Vilallonga, Barcelona (ES); Mar Hernández-Guillamón, Barcelona (ES); Mercedes Unzeta López, Barcelona (ES)

(73) Assignee: Universitat Autonoma de Barcelona, Bellaterra-Barcelona (ES)

( * ) Notice: Subject to any disclaimer, the term of this patent is extended or adjusted under 35 U.S.C. 154(b) by 104 days.

(21) Appl. No.: 13/062,205

(22) PCT Filed: Sep. 2, 2009

(86) PCT No.: PCT/ES2009/070362
§ 371 (c)(1),
(2), (4) Date: Jun. 15, 2011

(87) PCT Pub. No.: WO2010/026272
PCT Pub. Date: Mar. 11, 2010

(65) Prior Publication Data
US 2012/0014939 A1    Jan. 19, 2012

(30) Foreign Application Priority Data
Sep. 3, 2008  (ES) .................................. 200802548

(51) Int. Cl.
*C12Q 1/26*    (2006.01)
*G01N 33/573*    (2006.01)

(52) U.S. Cl.
CPC .... *G01N 33/573* (2013.01); *G01N 2333/90638* (2013.01); *G01N 2800/22* (2013.01); *C12Q 1/26* (2013.01)

USPC ............................................................ 435/25

(58) Field of Classification Search
CPC ............................................................ C12Q 1/26
See application file for complete search history.

(56) References Cited

FOREIGN PATENT DOCUMENTS

| WO | 2006036220 | 4/2006 |
|---|---|---|
| WO | WO 2006036220 A2 | 4/2006 |

OTHER PUBLICATIONS

Ishizaki "Plasma Benzylamine Oxidase Acivity in Cerebrovascular Disease" European Neurology, 1990 vol. 30 (2), 104-107.*
Stepanyan "Changes in histamine content, histaminase activity and histaminpexic index in the blood in acute disorders of cerebral circulation" Zhurnal Nevropatologii i Psikhiatrii Imeni, 1978 vol. 78, No. 9 p. 1322-1326.*
Boomsma "Plasma Semicarbazide-sensitive amine oxidase in human (patho)physiology" Biochimica et Biophysica Acta, 2003, 1647, 48-54.*
Mongar "Potentiation of the Action of Histamine by Semicarbazide" Nature, 1951, 167, 232-233.*
Salmi "Human Vascular Adhesion Protein-1 (VAP-1) Plays a Critical Role in Lymphocyte-Endothelial Cell Adhesion Cascade Under Shear" Circulation Research, 200, 86, 1245-1251.*

(Continued)

*Primary Examiner* — Jon P Weber
*Assistant Examiner* — Charles Zoltan Constantine
(74) *Attorney, Agent, or Firm* — Gary J. Gershik; Cooper & Dunham LLP

(57) ABSTRACT

The invention provides a method for predicting a hemorrhagic disorder in a patient consisting determining amine oxidase and, particularly, VAP-1 in a sample from said patient. The invention also provides pharmaceutical compositions comprising an inhibitor of amine oxidase and an antithrombotic agent as well as the use of an inhibitor of amine oxidase for treatment of hemorrhagic disorders.

7 Claims, 7 Drawing Sheets

(56) References Cited

OTHER PUBLICATIONS

Weiss "Plasma Amine Oxidase: A Postulated Cardiovascular Risk Factor in Nondiabetic Obese Patients" Metabolism, vol. 52 Issue 6 (Jun. 2003), 688-692.*

Airas et al. "Vascular adhesion protein-1 in human ischaemic stroke", Neuropathology and Applied Neurobiology, 2008, vol. 34, pp. 394-402.

Castellanos et al., "Plasma Cellular-Fibronectin Concentration Predicts Hemorrhagic Transformation After Thrombolytic Therapy in Acute Ischemic Stroke", Stroke, 2004; vol. 35, pp. 1671-1676.

Castellanos & Serena, "Applicability of Biomarkers in Ischemic Stroke", Cerebrovasc SDis, 2007, 24 (Supp 1); pp. 7-5.

Cocho et al., "Pretreatment Hemostatic Markers of Symptomatic Intracerebral Hemorrhage in Patients Treated With Tissue Plasminogen Activator", Stroke, 2006, vol. 37, pp. 996-999.

Jalkanen and Salmi, "VAP-1 and CD73, Endothelial Cell Surface Enzymes in Leukocyte Extravasation", Arterioscler. Thromb. Vasc. Biol., 2008; vol. 28, pp. 18-26.

Millan et al., "Increased Body Iron Stores Are Associated With Poor Outcome After Thrombolytic Treatment in Acute Stroke", Stroke, 2007, vol. 38, pp. 90-95.

Montaner et al., "Matrix Metalloproteinase Expression is Related to Hemorrhagic Transformation After Cardioembolic Stroke", Stroke, 2001, vol. 32, pp. 2762-2767.

Montaner et al., "Matrix Metalloproteinase-9 Pretreatment Level Predicts Intracranial Hemorrhagic Complications After Thrombolysis in Human Stroke", Circulation, 2003, vol. 107, pp. 598-603.

Winbeck et al., "Prognostic Relevance of Early Serial C-Reactive Protein Measurements After First Ischemic Stroke", Stroke, 2002, vol. 33, pp. 2459-2464.

Yu et al., "Physiological and pathological implications of semicarbazide-sensitive amine oxidase", Biochim Biophys Acta, 2003, vol. 1647, pp. 193-199.

International Search Report issued by the International Searching Authority (ISA/O.E.P.M.) on Dec. 23, 2009 in connection with International Application No. PCT/ES2009/070362.

Notification of Transmittal of the International Preliminary Report on Patentability mailed Dec. 13, 2010 in connection with PCT International Application No. PCT/ES2009/070362, filed Sep. 2, 2009.

International Search Report issued Dec. 23, 2009 in connection with PCT International Application No. PCT/ES2009/070362, filed Sep. 2, 2009.

Airas L. et al. (2008) "Vascular Adhesion Protein-1 in human ischaemic stroke" Neuropathology and Applied Neurobiology 34:394-402.

Castellanos M. and Serena J. (2007) "Applicability of Biomarkers in Ischemic Stroke" Cerebrovascular Diseases 24:7-15.

Yu Ph et al. (2003) "Physiological and pathological implications of semicarbazide-sensitive amine oxidase" Biochimica and Biophysica Acta. 1647:193-199.

Carl J. Vaughan and Norman Delanty (1990) "Neuroprotective Properties of Statins in Cerebral Ischemia and Stroke" Stroke 30:1969-1973.

* cited by examiner

Expected Cum. Prob. / Observed Cum. Prob.

METHODS AND COMPOSITIONS FOR THE TREATMENT AND DIAGNOSIS OF HAEMORRHAGIC CONVERSION

This application is a §371 national stage of PCT International Application No. PCT/ES2009/070362, filed Sep. 2, 2009, claiming the benefit of Spanish Patent Application No. P20802548, filed Sep. 3, 2008, the contents of each of which are hereby incorporated by reference in their entirety.

This application incorporates-by-reference nucleotide and/or amino acid sequence which are present in the file named "110301_0206_82659_Sub_Seq_List_LAD.txt" which is 7 kilobytes in size, and which was created Mar. 3, 2011 in the IBM-PC machine format, having an operating system compatibility with MS-Windows, which is contained in the text file filed Mar. 3, 2011 as part of this application.

TECHNICAL FIELD OF INVENTION

The invention is related to the field of diagnostic methods and personalized therapies and, more particularly, the identification of biomarkers capable of distinguishing clinical conditions and allowing the individualized treatment of patients suffering from thromboembolic disorders.

BACKGROUND OF INVENTION

Cerebrovascular attack (CVA) or stroke is the third cause of death and the most common cause of permanent disability in the world. Stroke is a sudden interruption in the blood supply to the brain. About 80% of strokes are caused by an abrupt blockage of arteries leading to the brain (ischemic stroke). Other strokes are caused by bleeding into the brain tissue due to a blood vessel burst (hemorrhagic stroke). Ischemic strokes can further be divided into thrombotic and embolic strokes. Thrombotic strokes occur when a brain artery is blocked by a blood clot formed in the brain and account for approximately 50% of all strokes. Embolic strokes are caused by a thrombus, which is formed in a peripheral artery that travels to the brain where it produces ischemia. Other causes of reduction of brain blood flow are: perforating artery occlusion, intracranial artery stenosis with poor collateral circulation, arteritis, arterial dissection, venous occlusion, and anemia or significant hyperviscosity.

So far, the only treatment for ischemic stroke during arterial occlusion phase is the use of thrombolytic agents to recover brain perfusion. Particularly, the intravenous administration of tissue plasminogen activator (tPA) is the choice treatment for patients who have suffered an ischemic stroke. However, often, patients who have suffered a stroke and are treated with thrombolytic therapy suffer from the so-called "hemorrhagic transformation" (HT), which is characterized by a process of blood extravasations involving a high morbidity and mortality. Therefore, in order to facilitate the selection of patients so that they can benefit to a great extent from treatment with t-PA, it is necessary to identify those patients at high risk of suffering hemorrhagic transformation. Surnii T et a (Stroke, 2002; 33:831-836) and Montaner J et al. (Circulation, 2003, 107:598-603) have reported that patients having high risk of suffering hemorrhagic transformation show elevated levels of matrix metalloproteinase-9 (MMP-9) so that determination of MMP-9 levels can be used to predict the probability of hemorrhagic complications after thrombolytic therapy for stroke.

Millán et al (Stroke, 2007, 38:90-95) have reported that elevated intracorporeal iron and ferritin levels are correlated with a worse prognosis in patients who have suffered stroke and with a higher risk of suffering hemorrhagic transformation after thrombolytic therapy.

WO2006036220 describes that increased plasma levels of cellular fibronectin (c-Fn) are correlated with a worse prognosis in patients who have suffered stroke and with a higher risk of suffering hemorrhagic transformation after thrombolytic therapy.

Moreover, it has been demonstrated that patients who suffered hemorrhagic transformation presented lower levels of plasminogen activator inhibitor 1 (PAI-1) and higher levels of thrombin activable fibrinolysis inhibitor (TAFI), and that the combination of PAI-1<21.4 ng/mL and TAFI>180% levels had the best sensitivity and specificity for predicting the appearance of hemorrhagic complications (Ribóo et al, 2004, Stroke 35:2123-2127).

However, the use of MMP-9, cellular fibronectin and/or endogenous fibrinolysis inhibitors as markers for hemorrhagic transformation risk requires measurement of said protein expression levels, which usually requires an analysis time longer than that recommended to start thrombolytic therapy.

In addition, it has been reported that S100B protein may be used to determine the risk of hemorrhagic complications after thrombolytic therapy (Foerch, et al., 2007, Stroke, 38:2491-2495). However, the diagnostic sensitivity by using S100B levels as the only marker was rather low for this marker to be used as a reliable marker in clinical practice.

Therefore, there is a need for additional markers that allow predicting the propensity to suffer hemorrhagic transformation in patients who have suffered stroke and have been treated with thrombolytic therapy and, particularly, biomarkers that can be more rapidly determined since thrombolytic treatment provides better results when applied shortly after the stroke episode.

SUMMARY OF THE INVENTION

In a first aspect, the invention relates to a method for predicting hemorrhagic disorders in a patient comprising determining the levels of an amine oxidase in a sample from said patient, wherein elevated levels of SSAO in this sample with respect to a reference value are indicative of the fact that the patient shows a high probability of suffering a hemorrhagic condition.

In a second aspect, the invention relates to a method for selecting a personalized therapy for a patient who has suffered ischemic stroke comprising determining the levels of an amine oxidase in a sample from said patient, wherein low or similar amine oxidase levels in this sample with respect to a reference value are indicative of the fact that the patient is intended to be selected for treatment with an antithrombotic agent.

In a third aspect, the invention relates to a method for predicting the neurological evolution of a patient who has suffered stroke comprising determining the levels of an amine oxidase in a sample from said patient, wherein high amine oxidase levels in this sample with respect to a reference value are indicative of the fact that the patient is going to suffer a neurological worsening.

In a fourth aspect, the invention relates to a method for determining the therapeutic window of antithrombotic treatment in response to an ischemic stroke comprising determining the levels of an amine oxidase in a sample from said patient, wherein elevated levels of amine oxidasa in this sample with respect to a reference value is indicative of the fact that treatment with an antithrombotic agent should be applied early after stroke.

In a fifth aspect, the invention relates to a composition comprising an amine oxidase inhibitor and an antithrombotic agent.

In a sixth aspect, the invention relates to a pharmaceutical preparation comprising a therapeutically effective amount of a composition of the invention and a pharmaceutically acceptable excipient or carrier.

In a seventh aspect, the invention relates to a composition of the invention for the treatment of thromboembolic disorders.

In an eighth aspect, the invention relates to an amine oxidase inhibitor for the treatment of hemorrhagic disorders.

DETAILED DESCRIPTION OF THE INVENTION

Prediction Method for Hemorrhagic Disorder

Figure 3:
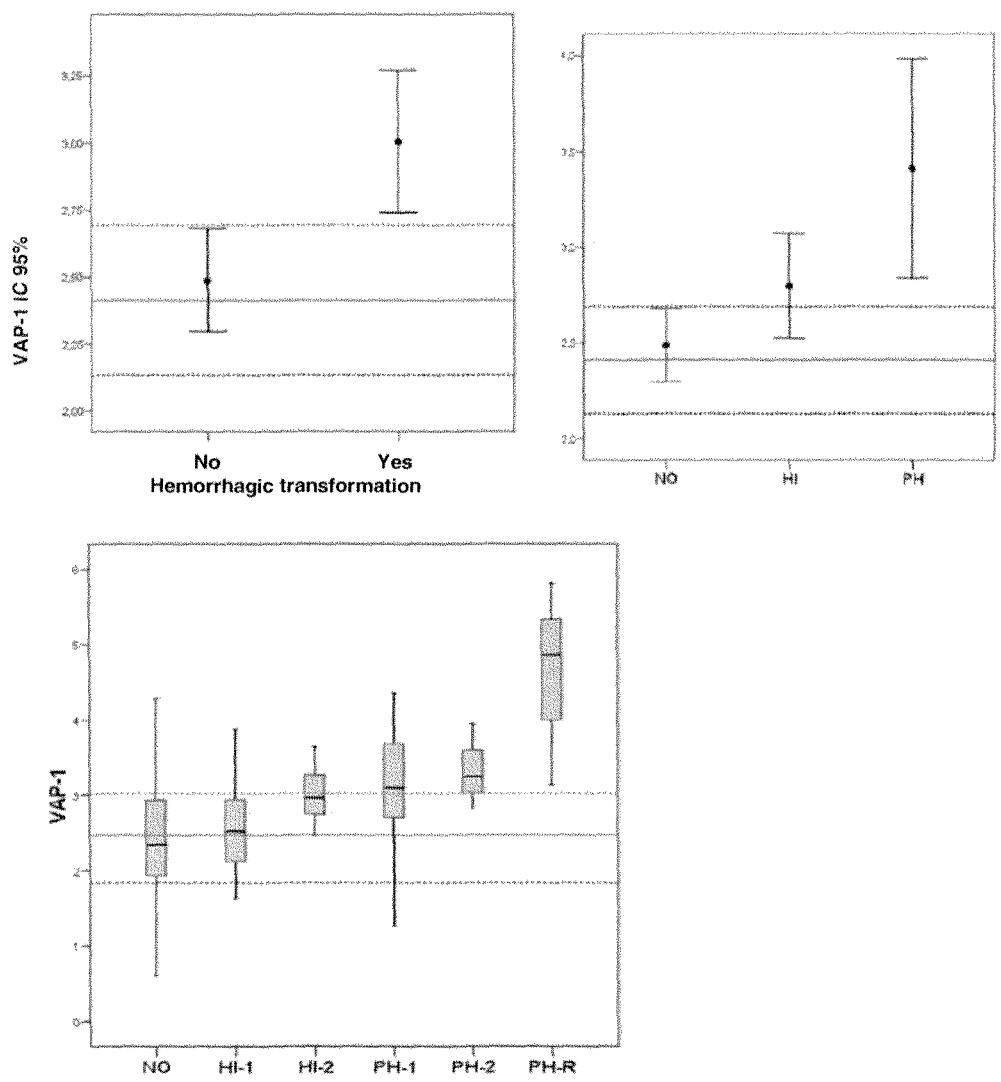
FIG. 3. Levels of VAP-1 activity according to the presence (A) and patterns of the main subtypes (B) of hemorrhagic transformation. Baseline VAP-1 relationships with all the subtypes of HT based on CT scan (C). A graduated response with elevated hemorrhage volumes was observed as the levels of VAP-1 activity increased. PH: Parenchymal hemorrhage; HI: Hemorrhagic infarction.

The authors of the present invention have observed unexpectedly that semicarbazide sensitive amine oxidase or SSAO is a good marker of the response to thrombolytic treatment in patients who have suffered ischemic stroke and that the elevated levels of VAP-1 activity are correlated to a higher probability of hemorrhagic transformation in these patients in a statistically significant manner. Thus, the results presented in the experimental part show that there is a significant increase in the baseline level of SSAO activity, presumably VAP-1, in the plasma of those patients who have suffered stroke and have been treated with intravenous tPA and later developed hemorrhagic transformation with respect to those patients who did not suffer hemorrhagic transformation, including both hemorrhagic infarctions and parenchymal hematomas within hemorrhagic transformation (FIG. 3A).

Therefore, in a first aspect, the invention relates to a method (hereinafter referred to as "first method of the invention") for predicting hemorrrhagic disorders in a patient comprising determining the levels of an amine oxidase in a sample from said patient, wherein elevated levels of this amine oxidase in this sample with respect to a reference value are indicative of the fact that the patient shows a high probability of suffering a hemorrhagic disorder. Thus, the results presented in FIG. 3 of the invention show as the activity of an amine oxidase, specifically, SSAO/VAP-1 is increased in the samples of patients who have suffered hemorrhagic transformation, including both hemorrhagic infarctions and parenchymal hematomas. Likewise, a correlation between VAP-1 levels and parenchymal hematoma degrees was observed. Different degrees of parenchymal hematoma were considered, for example, when 30% or less than 30% of hematoma on the infarcted area is observed (PH-1), when more than 30% of hematoma on the infarcted area is observed (PH-2) or when the blood clot appears at a distance far away from the infarcted area (PH-R).

Without wishing to be bound by theory, SSAO and, particularly, VAP-1 are thought to act by provoking an increase of vascular permeability in blood-brain barrier and, consequently extravasation of components from the bloodstream, thus facilitating access of the plasminogen activator to the central nervous system. In this way, in those patients who have been treated with a plasminogen activator and have suffered a hemorrhage, elevated levels of VAP-1 will provoke an increased concentration of the plasminogen activator in the central nervous system, resulting in an increase in the extent of hemorrhage or in the neurotoxic effect thereof.

As used herein, the term "prediction method" refers to a method for determining the probability that a patient suffers a hemorrhagic disorder. The person skilled in the art will estimate that the prediction may not be correct for 100% of patients under study. However, the expression requires that the prediction method provides correct results for a statistically significant portion of patients. Determination whether the method of the invention provides statistically significant predictions can be carried out by using standard statistical techniques such as the determination of confidence intervals, determination of p value, Student's t-test, Mann-Whitney test as described in Dowdy and Wearden, Statistics for Research, John Wiley & Sons, New York 1983. Suitable confidence intervals are at least 50%, at least 60%, at least 70%, at least 80%, at least 90%, at least 95%. p values are, preferably, 0.2, 0.1, 0.05.

The term "hemorrhagic disorder" is understood to mean, according to the present invention, a disorder in which an inappropriate blood clotting occurs, thus producing an excessive bleeding and including congenital hemorrhagic disorders, acquired hemorrhagic disorders caused by trauma, spontaneous hemorrhagic disorders or hemorrhagic disorders originated from thrombolytic treatment. Thus, the invention contemplates methods for predicting hemorrhagic conditions such as hemophilia A, hemophilia B, von Willebrand disease, idiopathic thrombocytopenia, deficiencies in one or more coagulation factors such as factor XI, factor XII, prekallikrein and high-molecular-weight kininogen, deficiencies associated with a clinically significant hemorrhage such as deficiencies in factor V, factor VII, factor VIII, factor IX, factor X, factor XIII, factor II (hypoprothrombinemia) and von Willebrand factor, vitamin K deficiency, alterations in fibrinogen such as afibrinogenemia, hypofibrinogenemia and dysfibrinogenemia, a deficiency in alpha 2-antiplasmin and excessive bleeding due to kidney disease, liver disease, thrombocytopenia, platelet alteration, hematomas, internal hemorrhages, hemarthros, surgery, trauma, hypothermia, menstruation and pregnancy.

In a preferred embodiment, the hemorrhagic condition that can be predicted with the method of the invention is a parenchymal hemorrhage, i.e., a leakage of blood into the brain parenchyma (white or gray substance) which can sometimes present opening to ventricular system (intraventricular hemorrhage), subarachnoid space (subarachnoid hemorrhage) or subdural space (subdural hemorrhage) or any other blood extravasation in the brain.

In another preferred embodiment, the hemorrhagic condition that can be predicted with the method of the invention is hemorrhagic transformation after a thrombolytic disease and treatment with an antithrombotic agent.

Thrombolytic diseases that can result in hemorrhagic transformation in the brain include cerebrovascular accident (stroke), acute myocardial infarction, massive pulmonary embolism and the like. In case the thromboembolic disease preceding the hemorrhagic episode is stroke, it can be of ischemic type caused by a atherosclerotic vascular disease, hypertensive vascular disease, hypertensive atherosclerotic vascular disease, amyloid angiopathy, vascular disease associated with inflammation caused, among others, by infections such as bacterial meningitis, TBC, syphilis, etc. or by a colagenopathy (LES, PAN, etc.), coagulation disorder, embolism, acute myocardial infarction, cardiac aneurysm, vasospasm, systemic hypotension, extrinsic vascular compression, artery dissection, venous thrombosis which can be caused in turn by vascular rupture, coagulopathy and the like.

Alternatively, thromboembolic diseases that may increase the risk of hemorrhagic transformation include deep venous thrombosis, pulmonary thromboembolism or acute myocardial infarction. Management of acute myocardial infarction involves the use of fibrinolytic agents because of their ability to obtain reperfusion and to regenerate blood flow when administered 12 hours within the onset of infarction. Suitable fibrinolytic agents for treating acute myocardial infarction include streptokinase, alteplase, reteplase, anistreplase and the like.

In case the hemorrhagic disorder is due to treatment with a thrombolytic agent after a stroke episode, said thrombolytic agent includes fibrinolytic agents such as tenecteplase, reteplase, plasmin, microplasmin, desmoteplase, V10153, glycoprotein IIb/IIIa antagonists with platelet disaggregating effects (abciximab, tirfiban), combinations of thrombolytic and antithrombotic drugs such as t-PA and tirofibran, t-PA and abciximab, repalase and abciximab, t-PA and eptifibatide and t-PA in combination with eptifibatide, aspirin and tinzaparin, combinations of thrombolytic and neuroprotective drugs as well as other non-pharmacological reperfusion strategies such as mechanical reperfusion strategies including intraarterial suction thrombectomy (a device for blood clot elimination and a device for suction thrombectomy), mechanical disruption (passing microguide wires, photoacoustic-laser emulsification and intracranial primary angioplasty), fibrinolysis strategies by endovascular ultrasound or externally applied ultrasound to potentiate enzymatic fibrinolysis.

Preferably, the antithrombolytic agent is a plasminogen activator. Plasminogen activators than can be used in the treatment of thromboembolic diseases and can lead to hemorrhagic transformation include tissue plasminogen activator (tPA), urokinase-like plagminogen activator (uPA) and streptokinase.

The term "amine oxidase" is understood to mean, according to the present invention, an enzyme capable of converting primary amines into the corresponding aldehydes and generating hydrogen peroxide and ammonium. The amine oxidases contemplated in the present invention include the amine-oxidase group containing copper and a topa quinone cofactor, which are generically denominated semicarbazide-sensitive amine oxidases (SSAO), but they do not contemplate the use of FAD-dependent amine oxidases (monoamine oxidases A and B and polyamine oxidase), as deduced from the fact that results were obtained in the presence of specific inhibitors of this type of enzymes. In a preferred embodiment, the amine oxidase used in the present invention as a biomarker is SSAO.

The term "SSAO" is understood to mean, according to the present invention, any family member of generically known enzymes, EC 1.4.3.6, which are characterized by (i) their ability to deaminate short-chain aliphatic or aromatic primary amines such as methylamine, aminoketone, allylamine, benzylamine, beta-phenyl-amine, tyramine, dopamine, mescaline, tryptamine, histamine in order to generate aldehydes, hydrogen peroxide and ammonium, (ii) the presence of a topa quinone group that acts as a cofactor and results from the post-translational modification of a tyrosine radical in the active site, (iii) the presence of copper in the active site and (iv) their sensitivity to inhibition by reagents that generate carbonyl groups such as semicarbazide, hydroxylamine, propargylamine, pyridoxamine, (+) mexiletine, B-24, FLA 336, MDL-72145, (E)-2-(4-fluorophenetyl)-3-fluoroallyilamine hydrochloride (MDL-72974A) or hydrazine derivatives such as iproniazide, phenelzine, procarbazine, hydralazine, carbidopa, benserazide, aminoguanidine and the like. The SSAO family includes enzymes AOC1, AOC2 and AOC3. AOC1 is the diamine oxidase found primarily in kidney, although it is also expressed in the liver, intestine and brain. The enzyme is involved in the catabolism of histamine, putrescine, and other polyamines. At the same time, the hydrogen peroxide and aldehydes resulting from polyamine metabolism have contributed to apoptotic cell death in brain injury. It has also been described that serum diamine oxidase activity is high during intestinal ischemia. AOC2 is a retina-specific amine oxidase. Preferably, the SSAO used in the present invention as a biomarker is AOC3, which is also known as vascular adhesion protein 1 (VAP-1). VAP-1 corresponds to the protein whose sequence is defined with access number Q16853 in UniProt (SEQ ID NO:1) and is formed by 763 amino acids, from which amino acids 27-763 form the extracellular domain. The present invention includes both the membrane-anchored VAP-2 form and the soluble version of the same resulting from release of the extracellular domain (amino acids 27-763) into the medium. In addition to the amine oxidase activity, VAP-1 is a protein capable of modifying the adhesive properties of endothelial cells thereby facilitating the adhesive capacity of lymphocytes.

Moreover, the method of the invention contemplates the use of functionally equivalent variants of VAP-1 as biomarkers in patients at risk of suffering a hemorrhagic episode. The term "functionally equivalent variant" is understood to mean all those proteins derived from VAP-1 sequence by modification, insertion and/or deletion or one or more amino acids, whenever the amine oxidase function and/or the promoting function of lymphocyte extravasation is substantially maintained. Preferably, variants of VAP-1 are (i) polypeptides in which one or more amino acid residues are substituted by a preserved or non-preserved amino acid residue (preferably a preserved amino acid residue) and such substituted amino acid may be coded or not by the genetic code, (ii) polypeptides in which there is one or more modified amino acid residues, for example, residues modified by substituent bonding, (iii) polypeptides resulting from alternative processing of a similar mRNA, (iv) polypeptide fragments and/or (iv) polypeptides resulting from VAP-1 fusion or the polypeptide defined in (i) to (iii) with another polypeptide, such as a secretory leader sequence or a sequence being used for purification (for example, His tag) or for detection (for example, Sv5 epitope tag). The fragments include polypeptides generated through proteolytic cut (including multisite proteolysis) of an original sequence. The variants may be post-translationally or chemically modified. Such variants are supposed to be apparent to those skilled in the art.

As known in the art, the "similarity" between two polypeptides is determined by comparing the amino acid sequence and the substituted amino acids preserved from a polypeptide with the sequence of a second polypeptide. The variants are defined to include polypeptide sequences different from the original sequence, preferably different from the original sequence in less than 40% of residues per segment concerned, more preferably different from the original sequence in less than 25% of residues per segment concerned, more preferably different from the original sequence in less than 10% of residues per segment concerned, more preferably different from the original sequence in only a few residues per segment concerned and, at the same time, sufficiently homologous to the original sequence to preserve functionality of the original sequence and/or ubiquitine (or ubiquitine-protein)-binding capacity. The present invention includes amino acid sequences which are at least 60%, 65%, 70%, 72%, 74%, 76%, 78%, 80%, 90%, or 95% similar or identical to the original amino acid sequence. The degree of identity between two polypeptides is determined using computer algorithms and methods which are widely known to those skilled in the art. The identity between two amino acid sequences is preferentially determined using BLASTP algorithm [BLAST-Manual, Altschul, S. et al., NCBI NLM NIH Bethesda, Md. 20894, Altschul, S., et al., J. Mol. Biol. 215: 403-410 (1990)].

As used herein the term "sample" refers to any sample collected from a patient showing a representative amount of SSAO with respect to body content so that the determination of SSAO levels in the sample can constitute a measure for SSAO body levels. If desired, in the case of determination of soluble SSAO levels, any type of fluid samples, for example serum, saliva, semen, sputum, cephalorachidian liquid (CRL), tears, mucus, sweat, milk, brain extracts and the like, can be employed. If desired, in the case of determination of membrane-bound SSAO, the use of solid tissue samples such as biopsy samples is preferred.

In a second stage, the first method of the invention comprises determining the levels of a semicarbazide sensitive amine oxidase (SSAO). —The phrase "Determining the levels of a semicarbazide sensitive amine oxidase (SSAO)", as used herein, means both protein levels and mRNA levels encoding said protein in a patient sample and the determination of said SSAO activity, whether the amine oxidase activity or the capacity of promoting lymphocyte adhesion to endothelial cells.

Determination of mRNA levels is performed by techniques well-known in the art, such as RT-PCR, Northern blot, etc.

Determination of protein SSAO may be performed using any conventional method. As a non-limitative example, SSAO levels may be quantified using antibodies capable of binding specifically to protein SSAO (or to respective fragments containing the antigen determinants) and subsequent quantification of the resulting antigen-antibody complexes. The antibodies to be used in this type of assays may be, for example, polyclonal serum, hybridomas supernatants or monoclonal antibodies, antibody fragments, Fv, Fab, Fab' and F(ab')2, scFv, diabodies, triabodies, tetrabodies and humanized antibodies. At the same time, labeled or non-labeled antibodies may be used. Illustrative but not limitative examples of markers that may be used include radioactive isotopes, enzymes, fluorophosphorus, chimioluminiscent materials, substrates or enzyme cofactors, enzyme inhibitors, particles, stains, etc. There is a wide variety of well-known assays which may be used in the present invention, where non-labeled antibodies (primary antibody) and labeled antibodies (secondary antibody) are used; among these techniques, Western-blot or immunotransference, ELISA (enzyme-linked immunosorbent assay), RIA (radioimmunoassay), competitive EIA (enzyme immunoassay), DAS-ELISA (double antibody sandwich ELISA), immunocytochemical and immunohistochemical techniques, protein biochip-based (or micromatrix-based) techniques including specific antibodies or colloidal precipitation tests using for example reactive strips. Other tests for detection and quantification of SSAP protein include affinity chromatography techniques, ligand binding assays, etc.

In a preferred embodiment, the invention comprises determining SSAO levels on the basis of SSAO activity measurement. The person skilled in the art will understand that SSAO function may be determined by measuring amine oxidase enzymatic activity. Amine oxidase function may be determined using methods well known to those skilled in the art, such as the method described in Example 1 of the invention which is based on the use of [$^{14}$C]-benzylamine as a substrate and described in detail by Fowler et al (Biochem. Pharmacol., 1981, 30:3329-3332). In addition, SSAO activity may be measured by fluorimetric or colorimetric methods, which are based on the detection of hydrogen peroxide produced during reaction. For example, the method described by Hotl et al. (Anal. Biochem., 1997, 244:384-392) which is based on the detection of quinone imine at 498 nm formed from the condensation of vanillic acid and 4-aminoantipyrine in the presence of hydrogen peroxide formed during the oxidation of SSAO substrate.

In the particular case of VAP-1, it is also possible to determine the levels of this protein by measurement of adhesion-promoting activity of lymphocytes to capillary endothelial cells. This activity may be quantified by adhesion assays of peripheral blood lymphocytes to a monolayer of endothelial cells as described by Salmi et al (Circ. Res., 2000, 86:1245-1251).

Therefore, in a preferred embodiment, determination of SSAO levels is performed by measuring VAP-1 activity in a patient sample.

Finally, the first method of the invention includes the step of comparing amine oxidase levels in a patient sample with a reference value. Thus, increased levels of amine oxidase in the reference sample are indicative of the fact that the patient is at high risk of suffering a hemorrhagic disorder. According to the present invention, amine oxidase levels are estimated to be high with respect to a reference value when the levels in the patient sample show an increase of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150% or more.

The first method of the invention contemplates the determination of amine oxidase levels on a patient sample whether isolatedly or jointly with one or more additional markers whose predictive value of risk factors for a hemorrhagic disorder is already known. In this way, it is possible to predict the risk of suffering a hemorrhagic disorder more precisely by combination of the values of amine oxidase levels and one or more additional markers. Thus, in a preferred embodiment, the determination of amine oxidase levels is carried out in parallel with the determination of at least a second marker. In preferred embodiments, the additional marker o markers that can be determined are selected from the group consisting of one or various markers of cellular fibronectin, ferritin, MMP-9, PAI-1, TAFI and S100B. Consequently, high plasma cellular fibronectin, ferritin, MMP-9, TAPI or S110b levels or low PAI-1 levels with respect to a reference value are indicative of the fact that the patient shows a high probability of suffering a hemorrhagic disorder.

Plasma levels of cellular fibronectin are essentially determined according to the method described in WO2006036220. Cellular fibronectin corresponds to a fibronectin variant synthesized by endothelial cells and differs from plasma fibronectin, which is produced primarily by hepatocytes. As cellular fibronectin is found mostly in vascular endothelial cells, elevated plasma levels of cellular fibronectin are usually indicative of endothelial damage and, therefore, a higher risk of hemorrhagic transformation after thrombolytic therapy. Determination of fibronectin levels is preferentially carried out using immunoassays such as those previously described for determination of amine oxidase, SSAO Or VAP-1 levels.

Determination of ferritin levels provides an estimation of the total body iron load, and its relationship to brain damage appears to be based on the generation of hydroxyl radicals from oxygen during reperfusion, the increase of excitotoxic damage and blood-brain barrier disruption. Determination of ferritin levels is essentially carried out according to the method described by Millán et al. (Stroke, 2007, 38:90-95) or using any of the abovementioned immunological methods for determination of amine oxidase, SSAO or VAP-1 levels.

MMP-9 levels may be determined by any of the methods known in the art, including the methods based on the enzymatic activity determination of MMP-9 using fluorescently marked substrates such as MMP-9 EnzoLyte 490, SensoLyte Plus 520, Biotrak or Medac assays. Alternatively, MMP-9 levels may be determined by different immunoassays such as those described by Montaner et al. (Circulation, 2003, 107: 598-603) or using any of the abovementioned assays for determination of amine oxidase, SSAO or VAP-1 levels. The correlation between MMP-9 levels and the probability of suffering a hemorrhagic disorder seems to be due to the capacity of MMP-9 of using any of the components of the basal layer of brain capillaries such as collagen IV, laminin or fibronectin as a substrate.

After an ischemic event, release of endogenous fibrinolysis inhibitors is produced into the bloodstream (Montaner et al, 2003, Stroke, 34:1038-1040), which might give rise to important interindividual differences in global fibrinolytic capacity, since they will block or potentiate t-PA-mediated fibrinolysis and development of hemorrhagic transformation. In support of this hypothesis, some studies have indicated that patients who suffered hemorrhagic transformation showed lower levels of plasminogen activator inhibitor 1 (PAI-1) and higher levels of thrombin activable fibrinolysis inhibitor (TAFI), and that the combination of PAI-1<21.4 ng/mL and TAFI>180% levels had better sensitivity and specificity in predicting the occurrence of hemorrhagic complications (Ribó et al, 2004, Stroke, 35:2123-2127). PAI-1 and TAFI are fibrinolysis inhibitors; PAI-1 is the principal endogenous inhibitor of t-PA, which is directly bound to t-PA and inhibits its fibrinolytic action. TAR is a recently discovered inhibitor that acts on fibrin limiting the activation of the fibrinolytic pathway. Determination of TAR levels may be essentially carried out according to the method described by Montaner et al. (ibid.) by ELISA using specific antibodies. Determination of PAI-1 levels is essentially carried out according to the method described by Ribó et al (ibid.) by ELISA using specific antibodies.

Recently, Foerch et al. (Stroke, 2007, 38:2491-2495) have described that protein S100B may be used as a prognostic factor of hemorrhagic complications after thrombolytic therapy. In the first moments after ischemic stroke (first hours), S100B is indicative of the blood-brain barrier function earlier than a marker of infarct size, since the latter is not yet determined at this moment. Protein S100B is found at a concentration much higher in cephalorachidian liquid than in peripheral blood, and the blood-brain barrier opening may allow the passage of the protein into serum. In a retrospective study, serum S100B concentrations in patients with stroke were analyzed before treatment with tPA for 6 h following the onset of symptoms. Serum S100B concentrations were higher in patients who developed hemorrhagic transformation, thereby S100B proved to be an independent predictive factor of hemorrhagic transformation. Determination of S100B levels may be essentially carried out according to the method described by Foerch, et al., (ibid.) using immunoluminometric assay.

Method for Selecting a Personalized Therapy in Patients Who have Suffered an Ischemic Stroke The authors of the present invention have revealed that determination of amine oxidase levels in patients who have suffered an ischemic stroke allows determining the probability that said patients suffer hemorrhagic transformation after being treated with a thrombolytic agent. Therefore, results allow selection of personalized therapies for patients who have suffered an ischemic stroke by means of the determination of amine oxidase levels. Thus, in another aspect, the invention relates to a method (hereinafter referred to as "second method of the invention") for selecting a personalized therapy in patients who have suffered an ischemic stroke, which comprises determining amine oxidase levels in a sample from said patient. If the amine oxidase levels in said sample are lower than or similar to a reference value, it is indicative of the patient's selection for treatment with an antithrombotic agent.

The different embodiments of the second method of the invention with regard to the type of amine oxidase that can be determined, the method for determination of amine oxidase levels, and the reference value are essentially the same as those used in the first method of the invention and have been described in detail herein.

According to the present invention, amine oxidase levels are estimated to be lower or similar with respect to a reference value when the levels in the patient sample show a decrease of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100% (absent).

In the same way as in the first method of the invention, the second method contemplates the simultaneous determination of one or more additional markers so that the reliability of personalized therapy can be enhanced. Thus, in a preferred embodiment, the second method of the invention comprises determining at least a second marker. In yet a more preferred embodiment, the second marker is selected from the group consisting of cellular fibronectin, ferritin and MMP-9, PAI-1, TAFI and S100B. Low or similar plasma cellular fibrinectin, ferritin, MMP-9, TAPI or de S110b levels and low PAI-1 levels with respect to a reference value are indicative of the patient's selection for treatment with an antithrombotic agent.

In a preferred embodiment, in the second method of the invention, the antithrombotic agent is a plasminogen activator, particularly, tissue plasminogen activator.

Determination of the different markers used in combination with SSAO levels is carried out as described in the first method of the invention.

Method for Predicting the Neurological Evolution of a Patient Who has Suffered a Stroke The authors of the present invention have revealed that amine oxidase levels in a sample of patients who have suffered a stroke are useful not only to determine the predisposition of patients to suffer hemorrhagic transformation in response to treatment with a thrombolytic agent, but also to determine the neurological evolution of patients. Thus, FIG. 6, attached herein, shows that elevated levels of VAP-1 after stroke are associated with neurological worsening. Thus, in a further aspect, the invention relates to a method (hereinafter referred to as "third method of the invention") for predicting the neurological evolution of patients who have suffered a stroke, which comprises determining amine oxidase levels in sample where elevated amine oxidase levels with respect to a reference value are indicative of that fact the patient is going to suffer a neurological worsening.

The term "neurological worsening" is understood to mean, according to the present invention, an increase of 4 points or more in the NIHSS (National Institutes of Health Stroke Scale) Score as described by Brott Ty Bogousslaysky J (N. Engl. J. Med. 2000, 343:710-722). On applying periodically this scale, some changes are identified as worsening or stability or improvement (a decrease of 4 points or more in the NIHSS score). Alternatively, neurological worsening may be determined by Rankin scale which value 0 indicates absence of symptoms, value 1 indicates absence of disabling symptoms, value 2 indicates mild disability, value 3 indicates moderate disability, value 4 indicates severe/moderate disability, value 5 indicates severe disability and value 6 indicates death.

The terms "amine oxidase", "amine oxidase levels", "sample", "reference value", "elevated levels" have already been defined for the first and second method of the invention.

In a similar way to the first and second method of the invention, the determination of amine oxidase levels is carried out in parallel with the determination or one or more additional markers, which are also indicative of the patient neurological evolution. Preferably, said additional marker or markers are determined from the group consisting of cellular fibronectin, ferritin, MMP-9, PAI-1, TAFI, S100B and a molecule implicated in inflammatory processes, particularly, IL-6 and ICAM-1 where elevated plasma levels of cellular fibronectin, ferritin, MMP-9, TAPI, S110b or the inflammation marker and/or low levels of PAI-1 with respect to a reference value are indicative of the fact that the patient is going to suffer neurological worsening.

In a preferred embodiment, the method of the invention allows prediction of the neurological evolution of a patient who has suffered a stroke as well as those patients who have suffered an ischemic stroke.

Determination of the different markers used in combination with SSAO levels is carried out as described in the first method of the invention.

Method for Determining the Therapeutic Treatment Window of an Antithrombotic Agent in Response to an Ischemic Stroke The results provided by the authors of the present invention allow prediction on the therapeutic window, in which, treatment with a thrombolytic agent after stroke may be beneficial despite the limited risk of developing hemorrhagic transformation. Thus, in a further aspect, the invention relates to a method for determining the therapeutic treatment window of an antithrombotic agent in response to an ischemic stroke, which comprises determining amine oxidase levels in a sample from said patient. If the amine oxidase levels in said sample are lower than or similar to a reference value, it is indicative of the fact that the therapeutic treatment window with the antithrombotic agent can be extended.

The term "therapeutic window" is understood to mean, according to the present invention, the conditions in which the administration of an antithrombotic compound is recommended after stroke so that the risk of hemorrhagic transformation can be minimized. Exclusion criteria for t-PA administration in patients with an ischemic stroke are Patients over 80 years old Presence of hemorrhage on computerized tomography (CT) scan History of brain hemorrhage An evolution time later than 3 hours after symptom onset or unknown onset time Minor symptoms or evident improvement before the start of infusion Severe stroke according to clinical criteria (NIHSS>25) or neuroimaging Seizure stroke onset Symptoms suggestive of subarachnoid hemorrhage although CT scan is normal Treatment with heparin within the previous 48 hours and elevated TTPa levels Previous stroke at any time point and concomitant history of diabetes Stroke within the previous 3 months Platelet count below 100,000/mm3

Blood glucose level below 50 mg/dL or above 400 mg/dL

Systolic blood pressure higher than 185 mmHg, diastolic blood pressure higher than 110 mmHg or need of aggressive measures for lower limits of arterial pressure Known hemorrhagic diathesis Oral anticoagulant treatment Recent evidence of severe bleeding History of intracranial hemorrhage History of subarachnoid hemorrhage by aneurysm rupture History of CNS injury (aneurysms, neoplasias, intracranial or medullary surgery)

Hemorrhagic retinopathy (e.g., diabetic retinopathy)

History of heart massage, childbirth or puncture on an inaccessible blood vessel within the previous 10 days Bacterial endocarditis, pericarditis Acute pancreatitis Ulcerative gastrointestinal disease documented within the previous 3 months, esophageal varices, known intestinal vascular malformations Neoplasia with increased bleeding risk Severe liver disease (liver failure, cirrhosis, portal hypertension, active hepatitis)

Major surgery or significant trauma within the previous 3 months

The term "extended therapeutic window" used herein means the extension of the limits of application of thrombolytic medication in patients in which said medication would be inadvisable due to a high risk of hemorrhagic transformation. Thus, in a preferred embodiment, the identification of low levels of SSAO or SSAO in combination with the levels of other markers allows, among others, the extension of the therapeutic window for thrombolytic therapy in patients who have suffered a stroke after more than 3 hours or in patients with contraindications (patients over 80 years old or patients with some of the symptoms mentioned in the exclusion criteria).

The terms "amine oxidase", "amine oxidase levels", "sample", "reference value", "elevated levels" have already been defined for the first and second method of the invention.

In the same way as in the other methods of the invention, it is possible to determine the therapeutic window on the basis of amine oxidase levels and one or more additional markers. Preferably, one or more additional markers are selected from the group consisting of cellular fibronectin, ferritin, MMP-9, PAI-1, TAFI and S100B. Low or similar plasma cellular fibrinectin, ferritin, MMP-9, TAPI or dS110b levels and high PAI-1 levels with respect to a reference value are indicative of the fact that the therapeutic window of treatment with an antithrombotic agent can be extended.

Compositions of the Invention

The results provided by the authors of the present invention have revealed that the risk of suffering hemorrhagic transformation in patients who have suffered a thromboembolic disorder and have been subjected to thrombolytic therapy might decrease considerably by combined administration of such thrombolytic agent and a SSAO inhibitor, since the tendency to suffer hemorrhagic transformation seems to be associated with an increase of VAP-1 activity. Thus, in another aspect, the invention relates to a composition comprising an amine oxidase inhibitor and an antithrombotic agent.

In a preferred embodiment, the amine oxidase inhibitors of the compositions of the invention are agents that specifically inhibit SSAO. In a yet more preferred embodiment, such inhibitors are agents that specifically inhibit VAP-1. Agents capable of inhibiting amine oxidase activity in general and, more particularly, SSAO and VAP-1 activity are widely known to those skilled in the art. These agents include hydrazine derivatives such as aryl(alkyl)hydrazines, arylalkylamines, propenyl- and proparylamines, oxazolidinones and halo-alkylamines, including without limitation, 3-halo-2-phenylallylamine, semicarbazide, hydroxylamine, propargylamine, aminoguanidine, pyridoxamine, (+)mexiletine, B-24 (3,5-diethoxy-4-aminomethylpyridine), amiflamine (FLA 336(+)), FLA336(−), FLA788(+), FLA668(+), MDL-72145 ((E)-2-(3,4-dimethyloxyphenyl)-3-fluoroallyiamine, MDL-72974A ((E)-2-(4-fluorophenethyl)-3-fluoroallylamine hydrochloride), iproniazide, fenelzine, procarbazine (N-isopropyl-alpha-(2-methylhydrazine hydrochloride)-p-toluamide), hydralazine, carbidopa, benserazide, aminoguanidine (pimagedine), 2-bromoethyiamine and hydrazine carboxylic compounds as well as pharmaceutically acceptable salts thereof.

Additional agents capable of inhibiting VAP-1 or other SSAO include, without limitation, those described in U.S. Pat. Nos. 6,982,286, 6,624,202, 6,066,321, US2007293548 and US2007066646; US20060128770 (thiazole derivatives), US20060025438, US20050096360, US20040259923, US20040236108 (carboxylic hydrazines), US20040106654, US20030125360, US20020173521 and US20020198189, Koskinen et al. (Blood, 2004, 103:3388-3395), Lazar et al. (Acta Pharma. Hungarica, 2004, 74:11-18), peptide inhibitors described by Yegutkin et al. (Eur. J. Immunol., 2004, 34:2276-2285), Wang et al. (J. Med. Chem., 2006, 49:2166-2173), sterified pectins such as those described by Hou et al. (J. Ag. Food Chem., 2003, 51:6362-6326), for example DE65T4, DE94T18, DE25T4 and DE94T4, and anti-VAP-1 antibodies such as those described in U.S. Pat. Nos. 5,580,780 and 5,512,442 and Koskinen et al. (Blood, 2004, 103:3388-3395), Arvilommi et al. (Eur. J. Immunol., 1996, 26:825-833), Salmi et al. (J. Exp. Med., 1993, 178:2255-2260) and Kirten et al. (Eur. J. Immunol., 2005, 35:3119-3130), vitamin B1 and derivatives such as those described in WO2008025870,2,3,4,6,8-pentamethoxyl-dibenzofurane as described in CN1931851, aminoglycoside antibiotics such as those described in WO05063261.

Other VAP-1 inhibitors include, without limitation, phenylhydrazine, 5-hydroxytryptamine, 3-bromopropylamine, N-(phenyl-allyl)-hydrazine HCl (LJP-1207), 2-hydrazinopyiridine, TNF-alpha., MDL-72274 ((E)-2-phenyl-3-chloroallylamine hydrochloride), MDL-72214 (2-phenylallylamine), mexiletine, isoniazide, an endogenous molecule (see Lizcano et al., 1990, J. Neurol. Trans., 32:323-326) including a molecule of approximately 500 to 700 MW (see Obata et al., 2000, Neurosci. Lett., 296:58-60), imipramine, maprotiline, zimeldine, nomifensine, azoprocarbazine, monomethylhydrazine, dl-alpha-methyltryptamine, dl-alpha-methylbenzylamine, MD780236 (Dostert et al., 1984, J. Pharmacy Pharmacol., 36:782-785), 2-(dimethyl(2-phenylethyl)silyl)methanamine, cuprozine, alkylamino derivatives of 4-aminomethylpyridine (Bertini et al., J. Med. Chem., 2005, 48:664-670), and kinuramine. Preferred inhibitors are those that selectively inhibit SSAO, i.e., they are at least 2 times more potent than monoamine oxidases. Inhibitors may be reversible, competitive, noncompetitive or irreversible.

Alternatively, the invention contemplates the use of compounds that act at the level of the cells in which VAP-1 is synthesized and cause a total or partial blockade of VAP-1 synthesis by acting at the level of the protein translation from mRNA.

Compounds capable of inhibiting SSAO expression and/or activity include antisense oligonucleotides, ribozymes, siRNA, inhibitory antibodies, aptamers and spiegelmers. Small interfering RNA (siRNA) agents are capable of inhibiting target gene expression by interfering RNA. siRNAs may be chemically synthesized, or may be obtained by in vitro transcription, o may be synthesized in vivo in target cell. Typically, siRNAs consist of a double-stranded RNA from 15 to 40 nucleotides in length and may contain a protuberant region 3' and/or 5' from 1 to 6 nucleotides in length. Length of protuberant region is independent from total length of siRNA molecule. siRNAs act by post-transcriptional degradation or silencing of target messenger.

siRNA may be denominated shRNA (short hairpin RNA) characterized because the antiparallel strands that form siRNA are connected by a loop or hairpin region. siRNAs are constituted by a short antisense sequence (19 to 25 nucleotides) followed by a loop of 5-9 nucleotides, and the sense strand. shRNAs may be encoded by plasmids or virus, particularly retrovirus and, more particularly, retrovirus and under the control of promoters such as U6 promoter for RNA polymerase III.

The siRNAs of the invention are substantially homologous to SSAO mRNA or this protein-coding genome sequence. The term "substantially honomogous" is understood to mean that siRNAs have a sequence sufficiently complementary or similar to target mRNA so that siRNA may be able to provoke mRNA degradation by RNA interference. Suitable siRNAs to provoke interference include siRNAs formed by RNA, as well as siRNAs containing chemically different modifications such as:

siRNAs in which the links between nucleotides are different from those appearing in nature, such as phosphorothioate links.

Stranded-RNA conjugates with a functional reagent, such as a fluorophoro.

Modification of the ends of RNA strands, particularly the end 3' end by the combination with different functional hydroxyl groups at 2'-position.

Sugar-modified nucleotides such as O-alkylated radicals at 2'-position such as 2'-O-methylribose or 2'-O-fluoribose.

Base-modified nucleotides such as halogenated bases (for example 5-bromouracil and 5-iodouracil), alkylated bases (for example 7-methyl-guanosine).

The siRNAs and shRNAs of the invention may be obtained using a series of techniques known to a person skilled in the art. For example, siRNA may be chemically synthesized from protected ribonucleoside phosphoramidites in a conventional DNA/RNA synthesizer. Alternatively, siRNA may be produced by recombinant dicer from plasmid and viral vectors, where the coding region of siRNA strand or strands is under operative control of RNA polymerase III promoters. RNase Dicer processes shRNA into siRNA in cells.

The SSAO region which is taken as a basis for the design of siRNA is not limitative and may contain a region of coding sequence (between the initiation codon and the termination codon) or, alternatively, may contain sequences from the 5' or 3' untranslated region, preferably from 25 to 50 nucleotides in length and in any position in 3' position with regard to the initiation codon. A procedure for siRNA design involves the identification of sequence motive AA(N19)TT wherein N may be any nucleotide in SSAO sequence and the selection of those that exhibit a high content in G/C. If said sequence motive is not found, it is possible to identify sequence motive NA(N21) wherein N may be any nucleotide.

In another embodiment, the compositions of the invention comprise antisense oligonucleotides specific to SSAO, i.e., molecules whose sequence is complementary to mRNA coding for SSAO, i.e., complementary to cDNA coding chain. The antisense oligonucleotide may be complementary to a complete coding region or a region of same including both the coding region and the 5' and 3' untranslated regions. The antisense oligonucleotides may consist of 5, 10, 15, 20, 25, 30, 35, 40, 45, 50 or more nucleotides in length. The antisense oligonucleotides may be obtained by chemical synthesis or by enzymatic binding reactions widely known to a person skilled in the art. For example, an antisense oligonucleotide may further contain modified nucleotides which increase its biological stability or the stability of the bicatenary DNA-RNA complexes formed between the antisense oligonucleotide and the target polynucleotide, such as phosphorothioate derivatives, peptide nucleic acids and acridine-substituted oligonucleotides. Modified oligonucleotides that may be used for the preparation of antisense nucleic acid include 5-fluorouracil, 5-bromouracil, 5-chlorouracil, 5-iodouracil, hypoxanthine, xanthine, 4-acetyl-citosine, 5-(carboxyhydroxylmethyl) uracil, 5-carboxymethylaminomethyl-2-thiouridine, 5-carboxymethyl-aminomethyl uracil, dihydrouracil, beta-D-galactosylqueosine, inosine, N6-isopentenyladenine, 1-methylguanine, 1-methyl inosine, 2,2-dimethylguanine, 2-methyladenine, 2-methylguanine, 3-methylcitosine, 5-methylcitosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocitosine, 5-methyl-2-thiouracil, 2-thiouracil, 4-thiouracil, 5-methyluracil, uracil-5-oxyacetic acid methyl ester, 5-methyl-2-thiouracil, 3-(3-amino-3-N-2-carboxypropyl)uracil, and 2,6-diaminopurine. Alternatively, the antisense nucleic acid may be produced biologically using an expression vector in which the antisense-oriented nucleic acid has been cloned.

Another group of compounds that may form part of the compositions of the present invention are catalytically active nucleic acids known as ribozymes. Ribozimes comprise a catalytic region and a second region whose sequence is complementary to target nucleic acid and confers substrate specificity on the ribozime. After the interaction between the ribozime and its substrate by hybridization and coupling between complementary regions of target nucleic acid and ribozime, an activation of the catalytic region is produced provoking the inter- or intramolecular rupture of target nucleic acid. Basic considerations for the design of ribozimes are widely known to a person skilled in the art (see, for example, Doherty and Doudna (Annu. Ref. Biophys. Biomolstruct. 2000; 30:457-75).

Another type of compounds that may form part of the compositions of the invention includes inhibitory antibodies. The term "inhibitory antibody" is understood to mean, according to the present invention, an antibody that is capable of binding to SSAO provoking the inhibition of its activity. Antibodies may be prepared using any method known to a person skilled in the art. Thus, polyclonal antibodies are prepared by immunization of an animal with the protein aimed to be inhibited. Monoclonal antibodies are prepared using the method described by Kohler, Milstein et al (Nature, 1975, 256: 495). Once antibodies capable of binding to SSAO are identified, those antibodies capable of inhibiting SSAO activity using the abovementioned assays for determination of SSAO activity will be selected. Suitable antibodies in the present invention include intact antibodies which comprise an antigen-binding variable region and a constant region, fragments "Fab", "F(ab')2" y "Fab'", Fv, scFv, diabodies and bispecific antibodies.

Other compounds capable of inhibiting SSAO expression that may form part of the compositions of the invention include aptamers and spiegelmers. Aptamers and spiegelmers are single-stranded or double-stranded D- or L-nucleic acids that specifically bind to the protein resulting in a modification of the biological activity of protein. Aptamers and spiegelmers are 15 to 80 nucleotides in length and, preferably, 20 to 50 nucleotides in length.

Antithrombotic agents that may be used in the compositions of the present invention include both thrombolytic compounds, i.e, compounds that are capable of dissolving blood clots such as psilocibin, t-PA (Alteplase or Activase), reteplase (Retavase), tenecteplase (TNKasa), anistreplase (Eminase), streptoquinase (Kabikinase, Streptase) or uroquinase (Abokinase), and anticoagulant compounds, i.e., compounds that prevent coagulation and include, without limitation, vitamin K antagonists (warfarin, acenocumarol, fenprocoumon and fenidione), heparin and heparin derivatives such as low molecular weight heparins, factor Xa inhibitors such as synthetic pentasaccharides, direct thrombin inhibitors (argatroban, lepirudin, bivalirudin and ximelagatran) and antiplatelet compounds that act by inhibition of platelet aggregation and, therefore, thrombus formation and include, without limitation, cyclooxygenase inhibitors (aspirin), adenosine diphosphate receptor inhibitors (clopidrogrel and ticlopidine), phosphodiesterase inhibitors (cilostazol), glycoprotein IIB/IIIA inhibitors (Abciximab Eptifibatide, Tirofiban and Defibrotide) and adenosine uptake inhibitors (dipiridamol). In a preferred embodiment, the antithrombotic agent that forms part of the compositions of the invention is a plaminogen activator. In a yet more preferred embodiment, the plasminogen activator is tPA (tissue plasminogen activator).

In addition, the combination therapy containing SSAO inhibitors and antithrombotic agents may be complemented with agents that inhibit other factors related to hemorrhagic transformation, for example matrix methalloproteinases (MMP-9), whose serum levels are high under conditions in which brain hemorrhage occurs after treatment with thrombolytic agents. Thus, the invention contemplates the combined use of SSAO inhibitors as above described, thrombolytic agents and MMP-9 inhibitors. In a preferred embodiment, MMP-9 inhibitor is BB-3103, Ro 31-9790, BB-1101, BB-2293, broad-spectrum MMP inhibitor GM-6001 (also denominated Galardin and Ilomastat), selective gelatinase inhibitor SB-3CT, as well as the agents described by Nakatani et at (Bioorganic & Medicinal Chemistry, 2006, 14:5402-5422), Mackarel et al (Am. J. Respir. Cell Mol. Biol., 1999, 20:1209-1219) and Yang et al. (J. Cerebral Blood Flow & Metabolism, 2007, 27:697-709), whose whole content is incorporated in the present invention. These additional agents may form part of the pharmaceutical composition or, alternatively, may be formulated as a separate pharmaceutical composition for its administration at the same time (simultaneous administration) as the pharmaceutical compositions of the invention or at different times (sequential administration) with regard to the pharmaceutical composition provided by this invention.

The therapeutic compositions of the present invention may be used for their combined, sequential or separate use with drugs that are useful in the treatment of acute ischemic stroke, such as the neuroprotective drugs, minocycline, citicholine, albumin, as well as antiinflammatory drugs and agents that avoid infiltration of neutrophils into brain parenchyma, as simvastatin, interferon-beta and the like.

For their medicinal use, the compositions of the invention constituted by a SSAO inhibitor and an antithrombotic agent may be found in a pharmaceutical composition. Thus, in a further aspect, the invention relates to a pharmaceutical preparation comprising a composition according to the invention in a mixture with a pharmaceutically acceptable excipient or carrier. The combination of compounds of the invention may be found as a prodrug, salt, solvate or clatrate, whether in an isolated dosage form or in combination with additional active agents. The combinations of compounds according to the present invention may be formulated in a mixture with a pharmaceutically acceptable excipient. Preferred excipients to be used in the present invention include sugars, starches, celluloses, gums and proteins. In a particular embodiment, the pharmaceutical composition of the invention will be formulated as a solid pharmaceutical dosage form (for example tablets, capsules, coated tablets, granules, suppositories, sterile crystalline or amorphous solids that can be reconstituted to provide liquid forms, etc.), liquid dosage form (for example solutions, suspensions, emulsions, elixirs, lotions, ointments, etc.) or semisolid dosage form (gels, pomades, creams and the like). The pharmaceutical compositions of the invention may be administered by any route, including, without limitation, oral, intravenous, intramuscular, intraarterial, intramedullary, intrathecal, intraventricular, transdermal, subcutaneous, intraperitoneal, intranasal, enteric, topical, sublingual or rectal route. A review of the different dosage forms of active ingredients and excipients to be used and their manufacturing processes is provided in "Tratado de Farmacia Galénica", C. Faulí and Trillo, Luzán 5, S. A. de Ediciones, 1993 and in Remington's Pharmaceutical Sciences (A. R. Gennaro, Ed.), 20$^{th}$ edition, Williams & Wilkins PA, USA (2000) Examples of pharmaceutically acceptable vehicles are known in prior art and include phosphate buffered saline solutions, water, emulsions, such as oil/water emulsions, different types of humectants, sterile solutions, etc. The compositions that comprise said vehicles may be formulated by conventional processes which are known in prior art.

The composition of the invention may be administered by different routes, for example, by intravenous, intraperitoneal, subcutaneous, intramuscular, topical, intradermal, intranasal or intrabronchial route, and can be administered locally, or systemically or directly at the target site. A review of the different dosage forms of active ingredients and excipients to be used and their manufacturing processes is provided in "Tratado de Farmacia Galénica", C. Faulí and Trillo, Luzán 5, S. A. de Ediciones, 1993 and in Remington's Pharmaceutical Sciences (A. R. Gennaro, Ed.), 20$^{th}$ edition, Williams & Wilkins PA, USA (2000).

In the particular case that the SSAO inhibitor is a nucleic acid (siRNA, antisense oligonucleotides, ribozymes, aptamers and epiegelmers), the pharmaceutical compositions may be formulated as a composition intended to for use in gene therapy; by way of illustration and not limitation, the pharmaceutical composition of the invention may contain a viral or nonviral vector, which comprises a polynucleotide of the invention or a gene construction of the invention. By way of illustration and not limitation, said vectors, may be viral, for example, based on retrovirus, adenovirus, etc., or nonviral such as ADN-liposome, ADN-polymer, ADN-polymer-liposome complexes, etc. [see "Nonviral Vectors for Gene Therapy", edited by Huang, Hung and Wagner, Academic Press (1999)]. Said vectors, which contain a polynucleotide or a gene construction of the invention, may be administered directly to humans or animals by conventional methods. Alternatively, said vectors may be used to transform, or transfect or infect cells, for example, mammal cells, including man, ex vivo, which subsequently will be implanted into a human body or an animal to obtain the desired therapeutic effect. For administration to a human body or an animal, said cells will be formulated in a suitable medium that will have no adverse influence on cell viability.

Dosage regimen will be determined by the physician and the clinical factors. As it is well known in medicine, dosage depends on several factors that include the physical features of the patient (age, size, sex), administration route, severity of disease, compound to be used and pharmacokinetic properties of the subject.

The term "therapeutically effective amount" is understood to mean, according to the present invention, the amount of an SSAO inhibitor and an antithrombotic agent sufficient to provoke a delay in hemorrhagic transformation occurrence in response to treatment of stroke with thrombolytic agents. Thus, the composition of the invention may contain an amount of antitumor agents ranging from 0.1 to 2,000 mg, preferably at the range of 0.5 to 500 mg and, more preferably, from 1 to 200 mg. Suitable doses of the compositions of the invention may range from 0.01 to 100 mg/kg boy weight, preferably from 0.1 to 50 mg/kg body weight, more preferably, from 0.5 to 20 mg/kg body weight. The composition may be administered at several times per day, particularly from 1 to 4 times daily.

The compositions of the invention may contain both components in a single container or both components may be physically separated in various containers, in which case, the composition is known as "kit of the invention". The term "kit" is understood to mean, according to the present invention, a product that contains different components of the invention which are packed to facilitate transport and storage. Suitable packing materials for providing the kit components include crystal, plastic (polyethylene, polypropylene, polycarbonate and the like), bottles, vials, paper, sachets and the like. In addition, the kits of the invention may contain instructions for simultaneous, sequential or separate administration of the different components in the kit. Instructions may be provided in printed material or in electronic support capable of storing instructions that can be read by a subject, such as electronic storage media (magnetic disks, magnetic tapes and the like), optical storage media (CD-ROM, DVD and the like). Additionally or alternatively, websites may be included to provide said instructions.

The compositions of the invention are useful for treating thromboembolic disorders, such as those described above. In a preferred embodiment, the thromboembolic disorder is stroke or myocardial infarction.

Pharmaceutical Compositions and Medical Uses of SSAO Inhibitors

The authors of the present invention have observed that VAP-1 levels are statistically significant in patients who have suffered a hemorrhagic episode after thrombolytic therapy for stroke, and such an increased activity may be at least partially responsible for hemorrhagic transformation. These observations unlock the door to a possible use of SSAO inhibitors and, in general, amine oxidase inhibitors for treating post-stroke hemorrhagic transformation and, in general, for treating hemorrhagic disorders. In another aspect, therefore, the invention relates to the use of amine oxidase inhibitors for treating hemorrhagic disorders.

In a preferred embodiment, the amine oxidase inhibitor is a SSAP inhibitor. In a yet more preferred embodiment, the SSAO inhibitor is a VAP-1 inhibitor. Suitable inhibitors for this purpose include the inhibitors defined above with regard to the compositions of the invention.

SSAO inhibitors may be formulated as pharmaceutical compositions as described above for the compositions of the invention, whether they are low-molecular-weight organic molecules, inhibitory antibodies or polynucleotides.

Hemorrhagic disorders that may be treated with SSAO inhibitors include, without limitation, all those coagulation disorders as defined above in the predictive method of the invention based on SSAO levels in a patient sample. In a preferred embodiment, the hemorrhagic disorder is a subsequent hemorrhagic transformation following thromboembolic disease after treatment with an antithrombotic agent. In a yet more preferred embodiment, the thromboembolic disease that precedes hemorrhagic transformation is a cerebrovascular accident. In a yet more preferred embodiment, SSAO inhibitors are used for treating hemorrhagic transformation in patients subjected to antithrombotic therapy in management of stroke.

The term "antithrombotic therapy" is understood to mean, according to the present invention, both pharmacological treatment for dissolving blood clots and mechanical treatment for promoting reperfused infarcted tissue. Therefore, SSAO inhibitors may be used in combination with fibrinolytic agents (tenecteplase, reteplase, plasmin, microplasmin, desmoteplase, V10153, glycoprotein IIb/IIIa antagonists with platelet disaggregating effects such as abciximab, tirfiban), in combination with thrombolytic and antithrombotic drugs (t-PA and tirofibran, t-PA and abciximab, repalase and abciximab, t-PA and eptifibatide and t-PA, eptifibatide, aspirin and tinzaparin), in combination with thrombolytic and neuroprotective drugs, in combination with antithrombotic therapies based on mechanical reperfusion strategies (intraarterial suction thrombectomy, a device for blood clot elimination and a device for suction thrombectomy), mechanical disruption (passing microguide wires, photoacoustic-laser emulsification and intracranial primary angioplasty), fibrinolysis strategies by endovascular ultrasound or externally applied ultrasound to potentiate enzymatic fibrinolysis.

Preferably, the antithrombolytic agent is a plasminogen activator, particularly tissue plasminogen activator (tPA).

The invention will be better understood by reference to the following examples, which illustrate but do not limit the scope of the invention.

EXAMPLES

Example 1

Methods
Study Population

Patients admitted to a university hospital emergency department with symptoms of acute stroke were prospectively studied. The target group consisted of patients who had been hospitalized for ischemic stroke within the first 3 hours after onset of symptoms. A total of 141 consecutive patients with nonlacunar stroke involving the vascular territory of middle cerebral artery (MCA) or basil artery were enrolled. All patients were subjected to urgent evaluation of the arterial tree by transcranial Doppler (TCD) ultrasound. Patients received t-PA at a standard dose of 0.9 mg/kg (10% by rapid intravenous injection and 90% by continuous infusion for 1 hour). Patients with known inflammatory or malignant disease were excluded. Finally, 140 patients were selected to undergo examination.

In addition, from the plasma library of tPA-treated patients (n=xx), 40 of these patients who had developed parenchymal hemorrhage and matched (by age, gender, etiology and extension of stroke) to the group of patients without hemorrhagic transformation (n=40) were selected. A control healthy group (n=30) was also evaluated in order to study VAP-1 values among the normal population.

Clinical Protocol

A history of vascular risk factors was obtained from each patient. In order to identify potential mechanisms for cerebral infarction, the following diagnostic tests were performed upon all patients: electrocardiography, thoracic radiography, carotid ultrasonography, full blood count, WBC differential count, and blood chemistry; when indicated, some patients were also subjected to special coagulation assays, transthoracic echocardiography and Holter monitoring. With this supporting information and neuroimaging data, determination of previously classified etiologic subtypes according to TOAST (Trial of Org 10172 in Acute Stroke Treatment) (Adams, H. P. et al., 1993, Stroke, 24:35-41) criteria was undertaken. Clinical examination was conducted on arrival in the emergency room, and 12, 24 and 48 hours after symptom onset. Stroke severity was assessed using the National Institute of Health Stroke Scale (NIHSS). Neurological improvement was defined as a decrease of >4 points in stroke scale score or neurological deterioration was defined as an increase of >4 points in stroke scale score or death after 48 hours (Brott T G, et al., 1992, *Stroke* 23:632-640).

Intravenous heparin was not administered during the course of the study. This study was approved by the Hospital Ethics Committee and all patients or their relatives gave informed consent.

Computed Tomography (CT) Scan

On admission, all patients underwent CT scan within the first 3 hours after stroke onset, which was repeated after 24-48 hours (or earlier when a rapid neurological deterioration occurred) in order to evaluate the presence of hemorrhagic transformation.

CT scans were analyzed by a skilled stroke neuroradiologist who was blinded to clinical data and VAP-1 results. The presence of type of hemorrhagic transformation was defined according to previously published criteria (Hacke W. et al., 1995, *JAMA*. 274:1017-1025 and Pessin M. et al., 1990, *Clin*

*Neuropharmacol.* 13:271-289). Hemorrhagic infarction (HI) was defined as a petechical infarction without space-occupying effect, and parenchymal hematoma (PH) was defined as hemorrhage with mass effect. For statistical analysis, both subtypes of HI and PH were considered together, (HI1, small petechiae along the margins of the infarct; HI2, more confluent petechiae within the infarcted area; PH1, hematoma involving ≤30% of the infarcted area with some slight space-occupying effect; and PH2, hematoma involving >30% of the infarcted area with substantial mass effect or PH-R, clot remote to the infarcted area). Symptomatic intracranial hemorrhage was defined as blood at any site in the brain on CT scan and documentation of clinical deterioration.

In this study, no patient with hypodensity involving >33 of the MCA territory was given tPA.

Determination of VAP-1 Activity

Peripheral blood samples were collected from all patients at the start of study (prior to tPA administration). From a sub-series of patients (n=7), serial samples were obtained to study the temporal profile of VAP-1 on baseline, 1 hour after tPA, 24 hours after symptom onset, hospital discharge, and 3 months after stroke. Sodium citrate tubes were used to collect blood and measure VAP-1 activity. Plasma was immediately separated by centrifugation at 3000 rpm for 15 minutes and stored at −80° C.

VAP-1/SSAO activity was determined radiochemically at 37° C. as previously described (Fowler, C. J. y Tipton, K. F., 1981, Biochem. Pharmacol. 30:3329-3332), using [$^{14}$C]-benzylamine 100 µM (3 mCi/mmol, Amersham, RU) as a substrate. Samples were preincubated for 30 minutes at 37° C. with L-deprenyl 1 µM to inhibit the possible contamination of platelet MAO-B. Reaction was carried out at 37° C. in a final volume of 225 µl of 50 mM Tris-HCl buffer, pH 9, and quenched by addition of 100 µl of 2M citric acid. Labeled products were removed in toluene/ethyl acetate (1:1, volume/volume) containing 0.6% 2,5-diphenyloxazole (PPO) (weight/volume) prior to scintillation liquid counting. Protein concentration was determined by the method of Bradford, and the resulting specific VAP-1/SSAO activity is expressed as pmol/min·mg of protein.

Statistical Analysis

Figure 1:
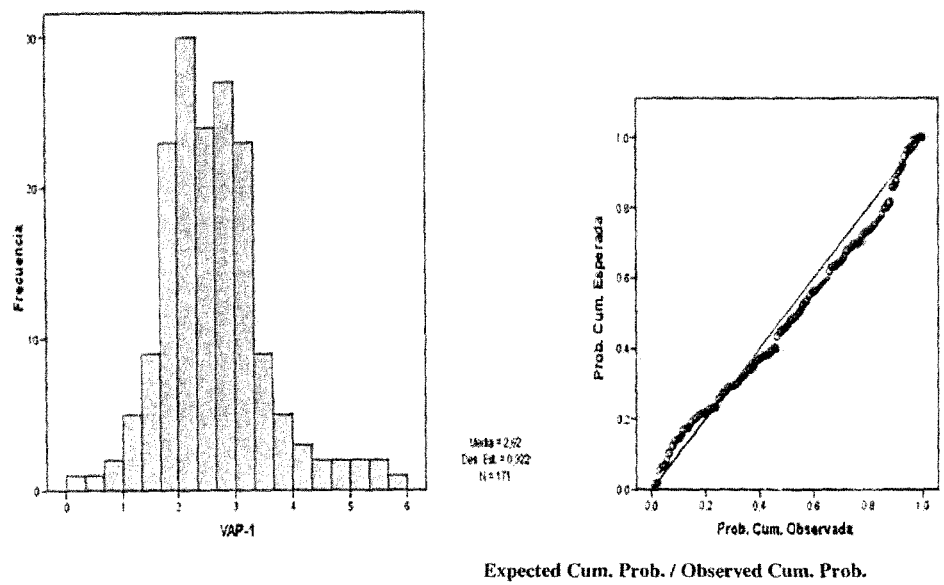
FIG. 1. Normal distribution of VAP-1 activity in the population under study (n=30 healthy control subjects+141 stroke patients) shown in the analysis of both histogram (A) and P-P plot (B).

Descriptive and frequency analyses were obtained and comparisons were made using the SPSS statistical package, version 14.0. Statistical significance for intergroup differences was assessed by Fisher's exact test for categorical variables and Student's t-test and ANOVA for continuous variables. Values of VAP-1 activity were distributed normally (Kolmogorov-Smirnov and P-P plot is shown in FIG. 1). Repeated-measures test (Friedman's test) was used for the evaluation of variations in the temporal profile of VAP-1 activity. Baseline levels of VAP-1 activity were used for subsequent analyses. When indicated, Mann-Whitney U test or Pearson's correlation coefficient were used. A receiver-operating characteristic (ROC) curve was configured to calculate the sensitivity and specificity of VAP-1 values and predict hemorrhagic transformation and PH. A logistic regression analysis was performed in order to identify independent prognostic factors for the subtypes of hemorrhagic transformation. P<0.05 was considered statistically significant.

Example 2

A total of 140 patients (46.1% women) with acute ischemic stroke were included in the study. Many of these patients showed involvement in MCA territory (n=132) and the remaining patients showed basilar artery occlusion (n=8) or posterior cerebral artery occlusion (n=1). Mean age was 70.85±11.8 years age (range 36-92 years). A total of 54.7% patients were hypertensive. 31.4% were dyslipidemic and 19.3% had a history of diabetes mellitus. NUBS score was 17 on admission (score range 3-29). TCD baseline detected a proximal MCA occlusion in 65.7% of the patients and a distal MCA occlusion in 34.3% of the patients. As far as stroke etiology is concerned, 45.7% of the patients had cardioembolism and 25.7% of the patients had atherothrombotic stroke.

Figure 2:
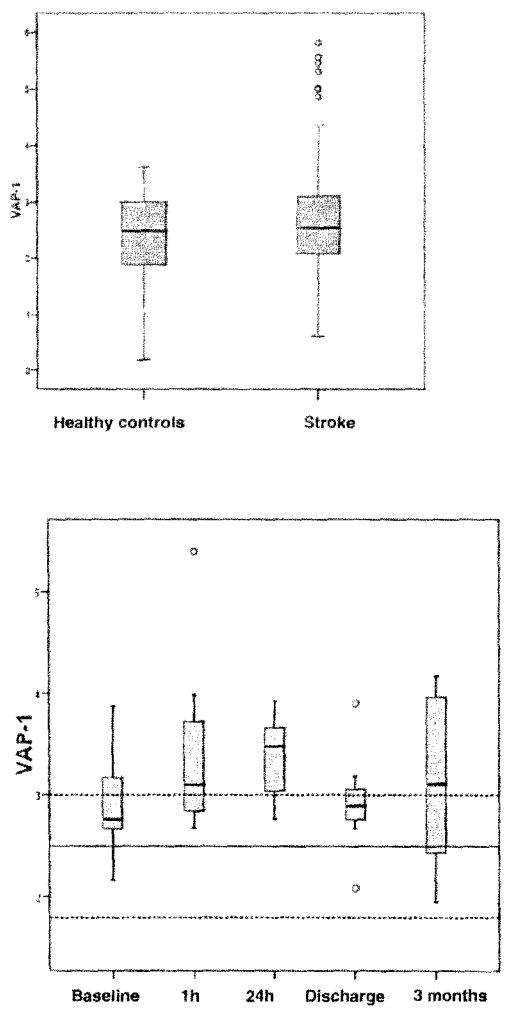
FIG. 2. A. Levels of VAP-1 activity are similar between healthy control subjects and stroke patients in the emergency room (<3 h). B. Temporal plasma profile of VAP-1 over the study period, which shows a trend towards increased level of VAP-1 during the first days. The dashed line indicates the reference interval for healthy control subjects.

Stroke patients had a mean baseline VAP-1 activity level=2.66, which was similar to VAP-1 level in healthy control subjects=2.40 (p=0.17, FIG. 2). Temporal VAP-1 profile after stroke is shown in FIG. 2. The highest VAP-1 level was found in 24-hour time point (p=0.055).

Aged patients had a higher level of VAP-1 level as shown in Table 1. There were no other differences between baseline VAP levels and variables such as gender, cardiovascular risk factors, or early infarction signs on CT scan. Only patients with auricular fibrillation had significantly higher baseline levels of VAP-1 (2.53±0.86 versus 2.86±1.06 ng/ml; p=0.051) and a correlation between VAP-1 levels and blood pressure levels was identified as shown in Table 1.

TABLE 1

Demographic factors and other baseline variables associated with stroke and their influence on VAP-1 level on patients at hospital arrival.

| | All patients | VAP-1 level | | |
|---|---|---|---|---|
| | (n = 141) | Yes | No | p |
| Qualitative data | | | | |
| Women | 65 (46.1%) | 2.76 | 2.57 | 0.24 |
| Hypertension | 63 (45.3%) | 2.68 | 2.61 | 0.67 |
| Dyslipemia | 44 (31.4%) | 2.50 | 2.72 | 0.20 |
| Diabetes mellitus | 27 (19.3%) | 2.65 | 2.65 | 0.97 |
| Previous stroke | 20 (14.4%) | 2.80 | 2.63 | 0.46 |
| Auricular fibrillation | 53 (38.1%) | 2.86 | 2.53 | 0.051 |
| Smokers | 23 (17.4%) | 2.56 | 2.62 | 0.74 |
| Proximal occlusion | 65.7% | 2.72 | 2.54 | 0.27 |
| Quantitative data | | | | |
| Age | 70.85 ± 11.8 | R = 0.19 | | 0.021 |
| Baseline score (NIHSS) | 17 | R = 0.05 | | 0.48 |
| Systolic BP, mmHg | 154 ± 27 | R = 0.22 | | 0.01 |
| Diastolic BP, mmHg | 84 ± 16 | R = 0.24 | | 0.006 |

The relationships between VAP-1 and qualitative data or the correlations between VAP-1 and quantitative data are shown.

Hemorrhagic transformation was observed in 48 (34.3%) patients [21 (15%) with HI-1, 11 (7.9%) patients with HI-2, 10 (7.1%) patients with PH-1, 3 (2.1%) patients with PH-2 and 3 (2.1%) with PH-R]. There was a significant increase of the baseline level of VAP-1 activity in patients who later developed hemorrhagic transformation (p<0.001, FIG. 3A). In addition, the highest baseline level of VAP-1 activity was found in patients with posterior PH and the lowest baseline level of VAP-1 activity in those patients without hemorrhagic transformation (PH: 3.41±-1.07, no HT: 2.48±0.92 and HI: 2.79±0.75; p=0.001) (FIG. 3B). There was a gradual response between baseline VAP-1 levels and the degree of hemorrhage CT scan (p<0.001, FIG. 3C).

Figure 4:
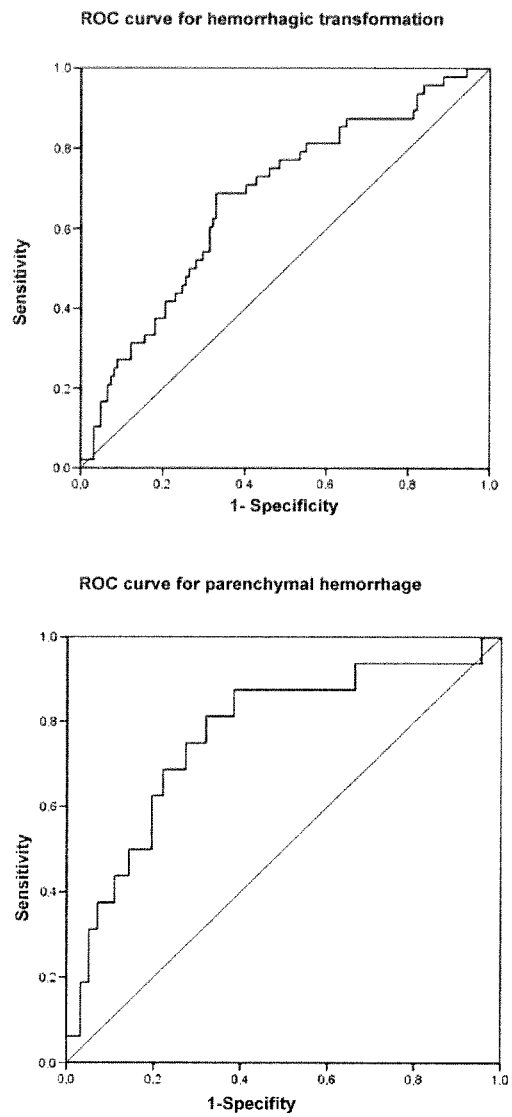
FIG. 4. ROC curves for identification of cut-off values for VAP-1 activity with the best sensitivity and specificity for the prediction of HT (A) or PH (B).
Figure 5:
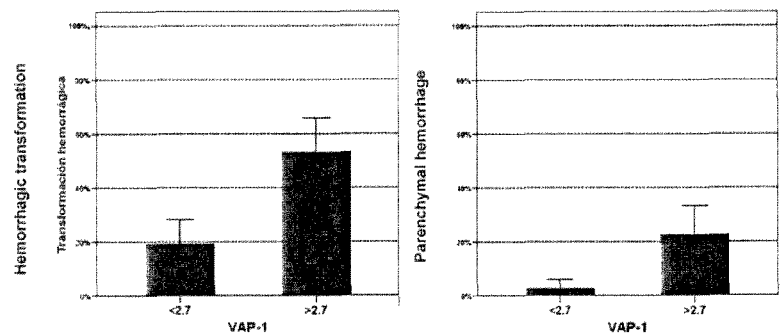
FIG. 5. Percentage of HT (A) and PH (B) when the selected cut-off values for VAP-1 activity were used.

The ROC curves used to identify the best cut-off values for the association of VAP-1 with hemorrhagic transformation and PH are shown in FIG. 4. A cut-off value of 2.7 for VAP-1 activity had sensitivity of 68.8% and specificity of 68.5% to detect the presence of hemorrhagic transformation with a positive predictive value=53.2% and a negative predictive value=88.8%. With regard to PH, the same cut-off value of 2.7 for VAP-1 had sensitivity of 87.5% and specificity of 61.3% to detect the presence of PH with a positive predictive value=62.26% and a negative predictive value=97.4%. However, a higher cut-off value of 3.7 for VAP-1 had sensitivity of 68.8% and specificity of 78.2% to detect the presence of PH with a positive predictive value=28.9% and a negative predictive value=95.1%. FIG. 5 shows hemorrhagic transformation and PH rates which are above cut-off values. High cut-off values for VAP-1 increases specificity but decreases sensitivity (i.e., VAP-1=5.0, 96.8% specificity for PH).

For HT, VAP-1 (>2.7) was the main baseline predictive factor for the appearance of HT [OR 5.84 (2.16-15.80), p=0.001] and it was also associated with hyperglycemia independently from hemorrhagic transformation [OR 1.03 (1.007-1.05), p=0.008]. Baseline VAP-1 level remained as the only prognostic factor independently associated to PH in the multiple logistic regression model using both the VAP-1 cut-off value of 2.7 [OR 11.18 (2.19-56.93), p=0.004] and the VAP-1 cut-off value of 3.07 [OR 8.94 (2.29-34.93), p=0.002].

Figure 6:
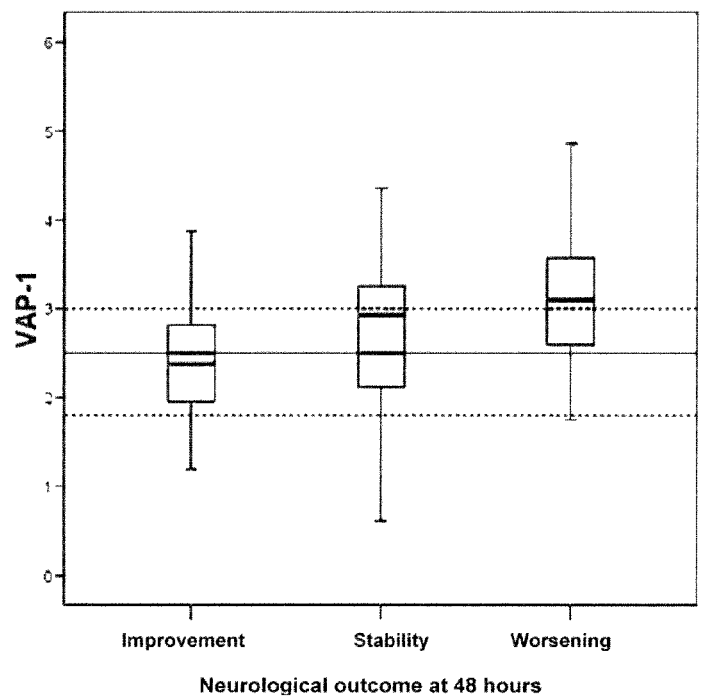
FIG. 6. Level of V activity with respect to the neurological outcome in the acute phase.
Figure 7:
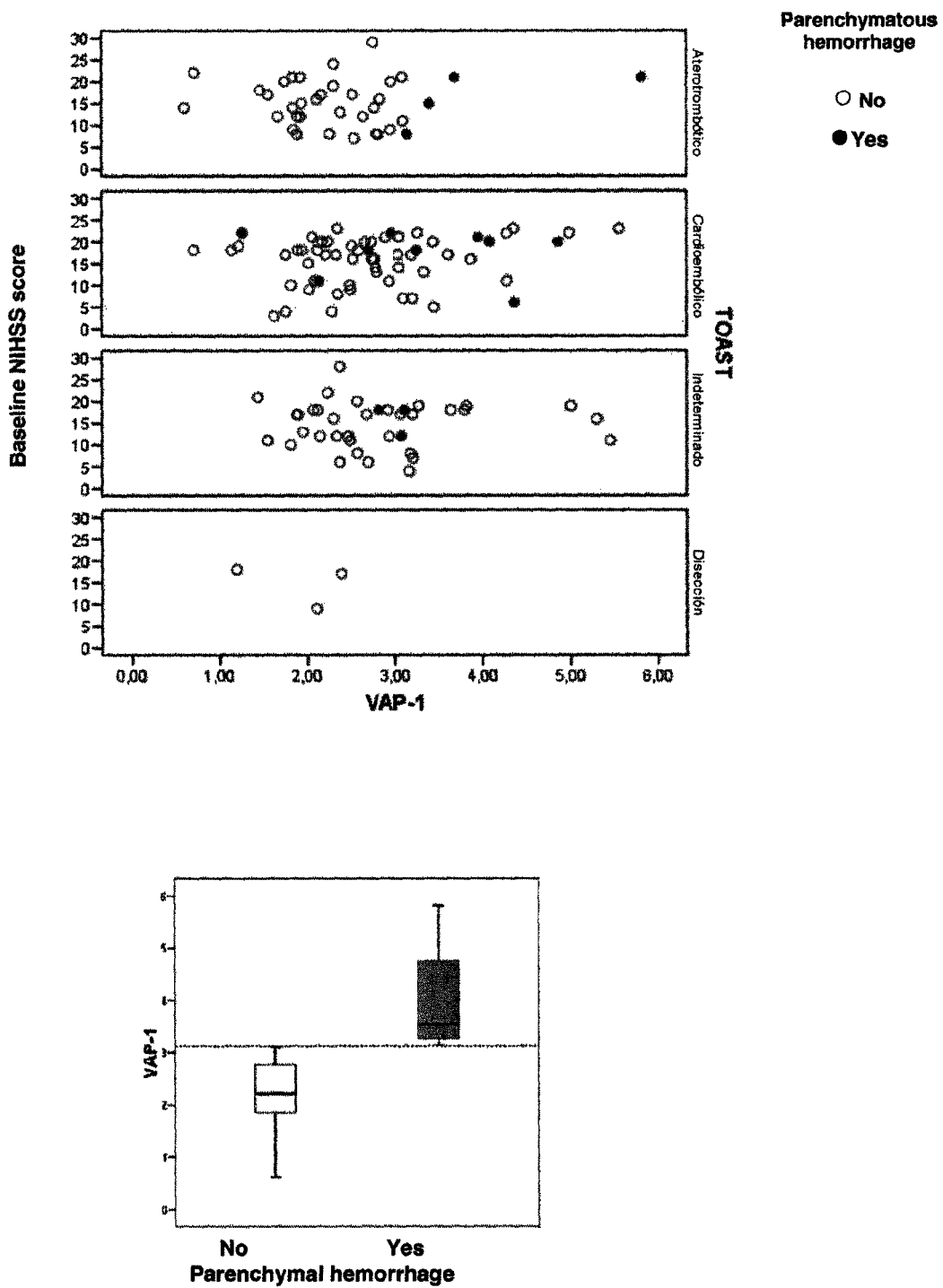
FIG. 7. Association of VAP-1 activity with parenchymal hemorrhage among the different subtypes of stroke. An impressive sensitivity (100%) and specificity (100%) were identified for a cut-off value of VAP-1=3.12 (dotted line) among atherothrombotic strokes.

Clinical assessment revealed that 15 patients (10.8%) worsened, 86 (61.9%) improved, and 38 (37.3%) remained stable during the first 48 hours after admission. Higher baseline VAP-1 levels were observed in patients with neurological worsening (p=0.032 as shown in FIG. 6). Analysis by stroke subtypes showed that VAP-1 predictor of PH appearance was even better among patients with atherothrombotic stroke (FIG. 7).

The invention claimed is:

1. A method of treating a patient for parenchymal hemorrhage in a patient who has suffered an ischemic stroke and has been treated with a thrombolytic agent comprising:
   a) measuring the level of VAP-1 in a sample of blood, plasma or serum from said patient by immunoassay or enzymatic assay;
   b) comparing the measured level of VAP-1 to a reference control sample value, wherein a statistically significant elevation of VAP-1 is indicative of increased risk of suffering a parenchymal hemorrhage; and,
   c) treating said patient for parenchymal hemorrhage if there is a statistically significant elevation in the measured level of VAP-1.

2. The method of claim 1, wherein the level of VAP-1 is determined by an enzymatic assay using [$^{14}$C]-benzylamine.

3. The method of claim 1, wherein the reference value is 2.7 ng/mL.

4. The method of claim 1, wherein the thrombolytic agent is plasminogen activator (t-PA).

5. The method of claim 2, wherein the thrombolytic agent is plasminogen activator (t-PA).

6. The method of claim 3, wherein the thrombolytic agent is plasminogen activator (t-PA).

7. A method as in any of the preceding claims, wherein step c) comprises administering an amine oxidase inhibitor.

* * * * *

UNITED STATES PATENT AND TRADEMARK OFFICE
CERTIFICATE OF CORRECTION

PATENT NO. : 8,906,642 B2  
APPLICATION NO. : 13/062205  
DATED : December 9, 2014  
INVENTOR(S) : Vilallonga et al.

Page 1 of 1

It is certified that error appears in the above-identified patent and that said Letters Patent is hereby corrected as shown below:

On the title page, item (73) should read

Universitat Autonoma de Barcelona, Bellarerra-Barcelona, Spain; and
Fundacio Institut de Recerca de L'Hospital Universitari Vall d'Hebron,
Fundacio Privada, Barcelona Spain.

Signed and Sealed this
Twenty-fourth Day of May, 2016

Michelle K. Lee
*Director of the United States Patent and Trademark Office*

SEQUENCE LISTING

<160> NUMBER OF SEQ ID NOS: 1

<210> SEQ ID NO 1
<211> LENGTH: 763
<212> TYPE: PRT
<213> ORGANISM: Human

<400> SEQUENCE: 1

Met Asn Gln Lys Thr Ile Leu Val Leu Leu Ile Leu Ala Val Ile Thr
1               5                   10                  15

Ile Phe Ala Leu Val Cys Val Leu Leu Val Gly Arg Gly Gly Asp Gly
            20                  25                  30

Gly Glu Pro Ser Gln Leu Pro His Cys Pro Ser Val Ser Pro Ser Ala
        35                  40                  45

Gln Pro Trp Thr His Pro Gly Gln Ser Gln Leu Phe Ala Asp Leu Ser
    50                  55                  60

Arg Glu Glu Leu Thr Ala Val Met Arg Phe Leu Thr Gln Arg Leu Gly
65                  70                  75                  80

Pro Gly Leu Val Asp Ala Ala Gln Ala Arg Pro Ser Asp Asn Cys Val
                85                  90                  95

Phe Ser Val Glu Leu Gln Leu Pro Pro Lys Ala Ala Ala Leu Ala His
            100                 105                 110

Leu Asp Arg Gly Ser Pro Pro Pro Ala Arg Glu Ala Leu Ala Ile Val
        115                 120                 125

Phe Phe Gly Arg Gln Pro Gln Pro Asn Val Ser Glu Leu Val Val Gly
    130                 135                 140

Pro Leu Pro His Pro Ser Tyr Met Arg Asp Val Thr Val Glu Arg His
145                 150                 155                 160

Gly Gly Pro Leu Pro Tyr His Arg Arg Pro Val Leu Phe Gln Glu Tyr
                165                 170                 175

Leu Asp Ile Asp Gln Met Ile Phe Asn Arg Glu Leu Pro Gln Ala Ser
            180                 185                 190

Gly Leu Leu His His Cys Cys Phe Tyr Lys His Arg Gly Arg Asn Leu
        195                 200                 205

Val Thr Met Thr Thr Ala Pro Arg Gly Leu Gln Ser Gly Asp Arg Ala
    210                 215                 220

Thr Trp Phe Gly Leu Tyr Tyr Asn Ile Ser Gly Ala Gly Phe Phe Leu
225                 230                 235                 240

His His Val Gly Leu Glu Leu Leu Val Asn His Lys Ala Leu Asp Pro
                245                 250                 255

Ala Arg Trp Thr Ile Gln Lys Val Phe Tyr Gln Gly Arg Tyr Tyr Asp
            260                 265                 270

```
Ser Leu Ala Gln Leu Glu Ala Gln Phe Glu Ala Gly Leu Val Asn Val
            275                 280                 285
Val Leu Ile Pro Asp Asn Gly Thr Gly Gly Ser Trp Ser Leu Lys Ser
290                 295                 300
Pro Val Pro Pro Gly Pro Ala Pro Pro Leu Gln Phe Tyr Pro Gln Gly
305                 310                 315                 320
Pro Arg Phe Ser Val Gln Gly Ser Arg Val Ala Ser Ser Leu Trp Thr
                325                 330                 335
Phe Ser Phe Gly Leu Gly Ala Phe Ser Gly Pro Arg Ile Phe Asp Val
            340                 345                 350
Arg Phe Gln Gly Glu Arg Leu Val Tyr Glu Ile Ser Leu Gln Glu Ala
        355                 360                 365
Leu Ala Ile Tyr Gly Gly Asn Ser Pro Ala Ala Met Thr Thr Arg Tyr
370                 375                 380
Val Asp Gly Gly Phe Gly Met Gly Lys Tyr Thr Thr Pro Leu Thr Arg
385                 390                 395                 400
Gly Val Asp Cys Pro Tyr Leu Ala Thr Tyr Val Asp Trp His Phe Leu
                405                 410                 415
Leu Glu Ser Gln Ala Pro Lys Thr Ile Arg Asp Ala Phe Cys Val Phe
            420                 425                 430
Glu Gln Asn Gln Gly Leu Pro Leu Arg Arg His His Ser Asp Leu Tyr
        435                 440                 445
Ser His Tyr Phe Gly Gly Leu Ala Glu Thr Val Leu Val Val Arg Ser
    450                 455                 460
Met Ser Thr Leu Leu Asn Tyr Asp Tyr Val Trp Asp Thr Val Phe His
465                 470                 475                 480
Pro Ser Gly Ala Ile Glu Ile Arg Phe Tyr Ala Thr Gly Tyr Ile Ser
                485                 490                 495
Ser Ala Phe Leu Phe Gly Ala Thr Gly Lys Tyr Gly Asn Gln Val Ser
            500                 505                 510
Glu His Thr Leu Gly Thr Val His Thr His Ser Ala His Phe Lys Val
        515                 520                 525
Asp Leu Asp Val Ala Gly Leu Glu Asn Trp Val Trp Ala Glu Asp Met
530                 535                 540
Val Phe Val Pro Met Ala Val Pro Trp Ser Pro Glu His Gln Leu Gln
545                 550                 555                 560
Arg Leu Gln Val Thr Arg Lys Leu Leu Glu Met Glu Glu Gln Ala Ala
                565                 570                 575
Phe Leu Val Gly Ser Ala Thr Pro Arg Tyr Leu Tyr Leu Ala Ser Asn
            580                 585                 590
His Ser Asn Lys Trp Gly His Pro Arg Gly Tyr Arg Ile Gln Met Leu
        595                 600                 605
Ser Phe Ala Gly Glu Pro Leu Pro Gln Asn Ser Ser Met Ala Arg Gly
    610                 615                 620
Phe Ser Trp Glu Arg Tyr Gln Leu Ala Val Thr Gln Arg Lys Glu Glu
625                 630                 635                 640
Glu Pro Ser Ser Ser Val Phe Asn Gln Asn Asp Pro Trp Ala Pro
                645                 650                 655
Thr Val Asp Phe Ser Asp Phe Ile Asn Asn Glu Thr Ile Ala Gly Lys
            660                 665                 670
Asp Leu Val Ala Trp Val Thr Ala Gly Phe Leu His Ile Pro His Ala
        675                 680                 685
```

```
Glu Asp Ile Pro Asn Thr Val Thr Val Gly Asn Gly Val Gly Phe Phe
    690             695             700
Leu Arg Pro Tyr Asn Phe Phe Asp Glu Asp Pro Ser Phe Tyr Ser Ala
705             710             715             720
Asp Ser Ile Tyr Phe Arg Gly Asp Gln Asp Ala Gly Ala Cys Glu Val
            725             730             735
Asn Pro Leu Ala Cys Leu Pro Gln Ala Ala Ala Cys Ala Pro Asp Leu
            740             745             750
Pro Ala Phe Ser His Gly Gly Phe Ser His Asn
        755             760
```